United States Patent
Barker et al.

(10) Patent No.: US 8,228,129 B2
(45) Date of Patent: Jul. 24, 2012

(54) PHOTONIC CRYSTAL RESONANT DEFECT CAVITIES WITH NANO-SCALE OSCILLATORS FOR GENERATION OF TERAHERTZ OR INFRARED RADIATION

(75) Inventors: Delmar L. Barker, Tucson, AZ (US); William R. Owens, Tucson, AZ (US); Patrick O. Kano, Tucson, AZ (US)

(73) Assignee: Raytheon Company, Waltham, MA (US)

( * ) Notice: Subject to any disclaimer, the term of this patent is extended or adjusted under 35 U.S.C. 154(b) by 909 days.

(21) Appl. No.: 12/265,930

(22) Filed: Nov. 6, 2008

(65) Prior Publication Data
US 2010/0108916 A1 May 6, 2010

(51) Int. Cl.
*H03B 5/32* (2006.01)
*G01J 3/44* (2006.01)

(52) U.S. Cl. .......... 331/107 A; 356/301; 250/341.1; 250/338.1; 359/573

(58) Field of Classification Search .......... 331/187, 331/107 A; 977/773; 356/301; 250/341.1, 250/338.1
See application file for complete search history.

(56) References Cited

U.S. PATENT DOCUMENTS

| | | | |
|---|---|---|---|
| 6,002,522 A | 12/1999 | Todori et al. | |
| 6,144,679 A | 11/2000 | Herman et al. | |
| 6,611,085 B1 | 8/2003 | Gee et al. | |
| 6,618,535 B1 | 9/2003 | Reynolds | |
| 6,690,023 B2 | 2/2004 | Silivra | |
| 6,744,552 B2 | 6/2004 | Scalora et al. | |
| 6,753,662 B1 | 6/2004 | Krafft | |
| 6,756,594 B2 | 6/2004 | George et al. | |
| 6,893,502 B2 | 5/2005 | Papadimitrakopoulos et al. | |
| 7,078,697 B2 | 7/2006 | Barker et al. | |
| 7,825,366 B2 * | 11/2010 | Barker et al. | 250/227.11 |
| 8,026,496 B2 * | 9/2011 | Barker et al. | 250/493.1 |

(Continued)

OTHER PUBLICATIONS

Chan et al., "Thermal emissions and design in one-dimensional periodic metallic photonic crystal slabs," 2006 The American Physical Society, Physical Rev. E 74, pp. 0166091-0166099.

(Continued)

*Primary Examiner* — Arnold Kinkead
(74) *Attorney, Agent, or Firm* — Eric A. Gifford

(57) ABSTRACT

A thermally powered source of IR or THz radiation combines low dimension nano-scale oscillators such as nano-wires and nano-tubes with micro-scale photonic crystal resonant defect cavities for efficient generation, coupling and transmission of electromagnetic radiation. The oscillators have M=0, 1 or 2 resonant dimensions on a micro-scale (approximately 1 um to approximately 1 mm) to emit radiation having a local peak at a desired wavelength in the IR or THz regions. The oscillators have at least one non-resonant dimension on a nano-scale (less than approximately 100 nm) to suppress vibration modes in that dimension and channel more thermal energy into the local peak. The photonic crystal defect cavities have N=1, 2 or 3 (N>M) resonant dimensions on the microscale with lengths comparable to the length of the oscillator and the desired wavelength to exhibit a cavity resonant that overlaps the local peak to accept and transmit emitted radiation. The energy from multiple oscillator/defect cavities pairs can be collected and transmitted by an internal waveguide or external mirrors and lens to a specified location where it is output. To improve coupling efficiency, the oscillators and defect cavities preferably exhibit a physical symmetry so that they are substantially "mode matched". The integration of nano-scale emitters with micro-scale photonic crystal defect cavities creates a new class of metamaterials that more efficient generate radiation.

24 Claims, 7 Drawing Sheets

U.S. PATENT DOCUMENTS

| | | |
|---|---|---|
| 2003/0219052 A1 | 11/2003 | Goodhue et al. |
| 2004/0013377 A1 | 1/2004 | Han |
| 2004/0075464 A1 | 4/2004 | Samuelson et al. |
| 2004/0113103 A1 | 6/2004 | Zhilkov |
| 2005/0121629 A1 | 6/2005 | Unterrainer et al. |
| 2005/0206020 A1 | 9/2005 | Baek et al. |
| 2005/0263269 A1 | 12/2005 | Kaneko et al. |
| 2006/0119853 A1* | 6/2006 | Baumberg et al. ............ 356/445 |

OTHER PUBLICATIONS

Nemilentsau et al., "Thermal radiation from carbon nanotubes in the terhertz range," 2007 The American Physical Society, Physical Rev. PRl.99, pp. 147403-1 through 4.

Iida, et al.., Enhanced generation of terahertz radiation using 3D photonic crystals with a planar defect, Proc. CLEO/QELS, Jun. 2002 (Baltimore), Section CM1.

Unterrainer et al. et al.; Cavity enhanced few cycle THz generation and coherent spectroscopy, Proc. CLEO/QELS, Jun. 2002 (Baltimore), Section CM1.

Han et al., Terahertz pulse propagation in a plastic photonic crystal fiber, Applied Physics Lett., 80 #15, Apr. 15, 2002, pp. 2634-2636.

Zhi-Yuan Li, Modified thermal radiation in three-dimensional photonic crystals, Phys. Rev. B 66, R241103 (2002), pp. 241103 to 1241103-4.

Lin et al., "Enhancement and suppression of thermal emission by a three-dimensional photonic crystal," Phys. Rev. B 62, R2243 (2000), pp. R2243-R2246.

* cited by examiner

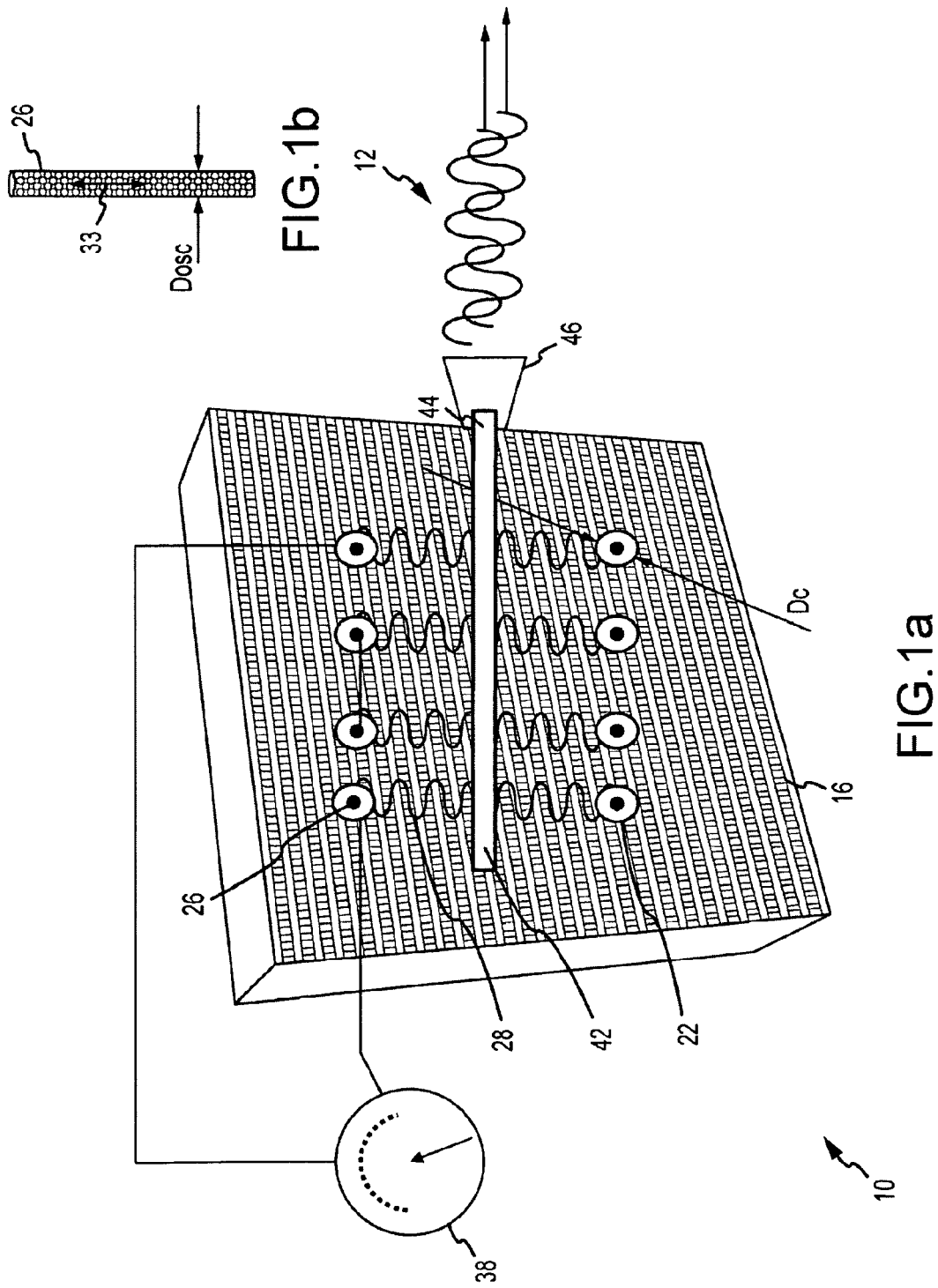

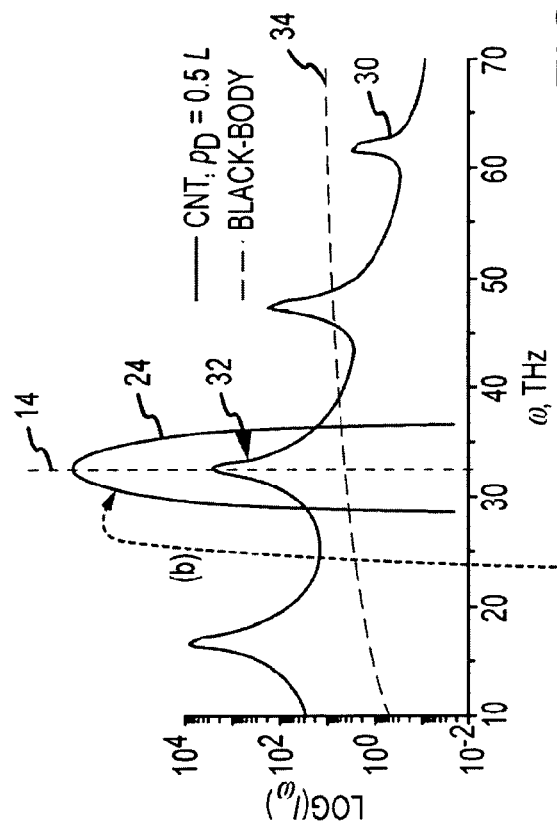
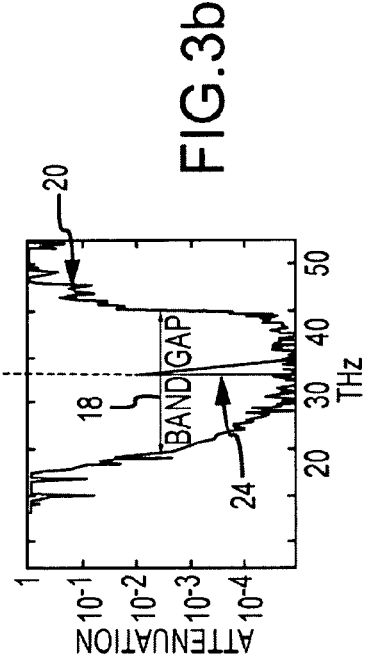
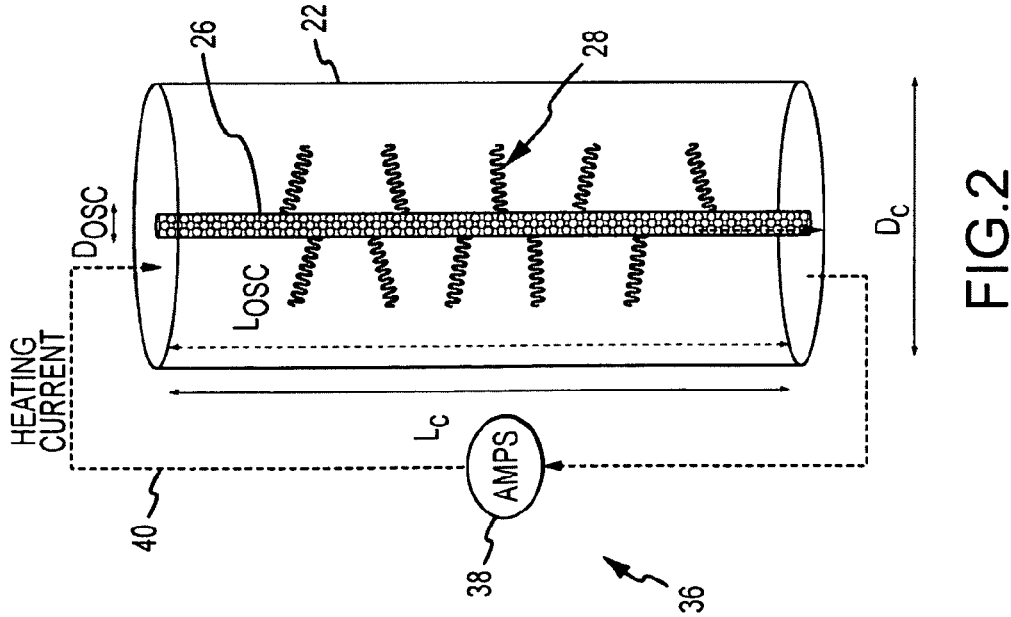
FIG. 3a
FIG. 3b
FIG. 2

PHOTONIC CRYSTAL RESONANT DEFECT CAVITIES WITH NANO-SCALE OSCILLATORS FOR GENERATION OF TERAHERTZ OR INFRARED RADIATION

BACKGROUND OF THE INVENTION

1. Field of the Invention

This invention relates to thermally powered terahertz (THz) and infrared (IR) radiation sources and more specifically to the integration of thermally powered low-dimensional nano-scale oscillators such as nanowires and nanotubes that emit radiation with micro-scale resonant defect cavities in photonic crystals to efficiently select, collect and transmit the emitted radiation in a specified narrow band.

2. Description of the Related Art

THz-frequency radiation, in the frequency region from 300 GHz to 10 THz, has been relatively unexploited compared to the adjacent radio frequency (RF) and IR spectral bands. This is largely because of transmission difficulties due to absorption by atmospheric water vapor but also due to a lack of practical radiation sources. In recent years there has been a significant growth of interest in applications of this previously underutilized portion of the electromagnetic spectrum. These applications include active short range imaging systems for concealed weapon detection or driving aids in dust or sand storms. The shorter wavelengths provide higher image resolution than is possible with traditional radar systems operating at radio frequencies. At longer ranges, the THz band is very useful for wide bandwidth space-based communications, high-resolution imaging of rotating satellites from another space-based platform and other space object surveillance applications. The lack of atmospheric attenuation at high altitudes permits use of THz radiation.

Spectroscopy is another application area for THz radiation. Many biological agents have abundant and easily recognized resonances in the THz region. From simple content analysis (material identification by exciting, then detecting molecular vibrational and rotation states) to spectroscopic imaging of trace clouds of biological agents, the THz spectrum promises to open many applications in the bio-detection area. Mounting a THz system on an unmanned aerial vehicle may make it possible to detect and map biological and certain chemical warfare agents on a battlefield. Researchers in the U.K. recently reported that THz radiation is 100% successful in detecting skin cancer, but they don't yet understand how (Scott, W. B., *Potential applications of terahertz signals spur scientists to explore RF/light border region*, Aviation Week & Space Technology, Jun. 21, 2004, page 68). Passive THz systems have also been used in astronomy to map molecular clouds in the galaxy.

One of the major bottlenecks for the successful implementation of THz-frequency systems is the limited output power of conventional THz sources. Most systems produce THz radiation via optical techniques, but those require massive lasers, complex optical networks and cooling systems. Some of the THz sources reported in the literature include optically pumped THz lasers, time-domain spectroscopy, backward wave oscillators, solid-state amplifiers combined with direct multipliers, and photo-mixers (Iida, M. et al., *Enhanced generation of terahertz radiation using 3D photonic crystals with a planar defect*, Proc. CLEO/QELS, June 2002 (Baltimore), Section CM1; Unterrainer, K. et al.; *Cavity enhanced few cycle THz generation and coherent spectroscopy*, Proc. CLEO/QELS, June 2002 (Baltimore), Section CM1; Han, H., Park, H., Cho, M., and Kim, J., *Terahertz pulse propagation in a plastic photonic crystal fiber*, Applied Physics Lett., 80 #15, 15 Apr. 2002). The different sources have disadvantages including limited output power; excessive cost, size and weight; poor reliability and limited frequency agility.

Three dimensional solid objects emit electromagnetic radiation in a spectral distribution which is described by the Planck equation for any given temperature of the object. This thermal spectral distribution is broad and continuous and peaks in the infrared (IR) band for room temperature objects, with surface emissivity variations providing the only deviation from the Planck distribution.

It is well known that an object's Planck blackbody radiation spectrum may be strongly modified when the object is a photonic crystal with a band gap positioned around the peak (e.g., 5-10 μm) of the Planck spectrum. Several theoretical and experimental papers in this area have been published with very interesting results including Zhi-Yuan Li, Phys. Rev. B 66, R241 103 (2002) and S-Y. Lin, et al, Phys. Rev. B 62, R2243 (2000).

U.S. Pat. No. 7,078,697 recites the use of photonic crystals to shift the thermal emission peak associated with the standard Planck blackbody spectral distribution from the IR band to the THz region. The photonic crystal core is designed to shift the photon density of states (DOS) such that the thermal radiation from the broad IR Planck peak shifts to a sharp peak in the THz region (0.3-10 THz). The photonic crystal core is combined with a waveguide and power combining structure so that the radiated THz energy is efficiently collected and directed to an output antenna. More specifically, a plurality of defect cavities can be formed in the photonic crystal layer to collect and concentrate the radiation in a limited bandwidth. The defect cavities then couple the radiation to an adjacent waveguide that directs the radiation to the output antenna.

Theoretical studies of one dimensional objects indicate a less smooth spectral distribution of thermal radiation from the objects. The one dimensional structures (compared to the radiation wavelengths involved) have restricted vibrational modes that channel more thermal energy into useful frequencies. Chan et al. "Thermal emission and design in one-dimensional periodic metallic photonic crystal slabs", Physical Review E 74, Jul. 26, 2006 presents a framework for understanding the physical phenomena that drive thermal emission in one-dimensional periodic metallic photonic crystals. A. M. Nemilentsau et al "Thermal Radiation From Carbon Nanotube in Terahertz Range" Physics Rev. Lett. 99, 147403 Oct. 5, 2007 theoretically investigates the thermal radiation from an isolated finite-length carbon nanotube (CNT) both in near- and far-field zones. The formation of the discrete spectrum (See FIG. 1(*b*)) in metallic CNTs in the terahertz range is demonstrated due to the reflection of strongly slowed-down surface-plasmon modes from CNT ends.

SUMMARY OF THE INVENTION

The present invention provides a thermally powered source of IR or THz radiation that combines nano-scale oscillators with micro-scale photonic crystal resonant defect cavities for efficient generation, coupling and transmission of electromagnetic radiation.

In an embodiment, a source of radiation for a specified band of wavelengths comprises a photonic crystal that exhibits a band gap coincident with the specified band such that a wavelength within the band gap is substantially confined in at least one dimension within the photonic crystal. At least one void defect cavity substantially within the photonic crystal exhibits a cavity resonance within the band gap in N dimensions where N is an integer of value 1, 2 or 3. An oscillator substantially within the void defect cavity in the crystal resonates in M dimensions where M is an integer less than N of value 0, 1 or 2 to generate electromagnetic radiation having a spectrum that exhibits at least one local peak. The one local peak overlaps the cavity resonance so that the cavity accepts and transmits the electromagnetic radiation in the local peak. Means heat the oscillator to increase the electromagnetic radiation.

In an embodiment, the oscillator may, for example, be a nano-scale structure in which the resonant dimensions are on a micro-scale (1 um to 1 mm) to resonate in a specified narrow band in IR or THz regions and the non-resonant dimensions are on a nano-scale (<100 nm) so that vibrational modes are suppressed in the specified narrow band. The resonant dimensions of the photonic crystal defect cavity would also be comparable to the desired emission wavelength in the micro-scale. Boundary conditions should be satisfied between the nanostructure oscillators and the micro structure photonic crystal to ensure mode matching and efficient coupling of the emitted radiation.

In another embodiment, the source further comprises a plurality of oscillators substantially within a respective plurality of void defect cavities substantially within the photonic crystal and a waveguide substantially within the photonic crystal to accept and transmit electromagnetic radiation from the plurality of void defect cavities to a specified location for emission, for example, via an antenna. The waveguide suitably comprises adjacent void defect cavities that do not include oscillators. The total surface area of the plurality of void defect cavities that include oscillators is greater than the surface of the photonic crystal itself.

In another embodiment, the source is configured with a symmetry so that the oscillator generates electromagnetic radiation in a first mode and the void defect cavity accepts radiation in a second mode in which the first and second modes substantially match. A 1-D oscillator within a 3-D cylindrical void defect cavity are mode matched. The 1-D oscillators may be positioned axially and/or radially to match different modes of the defect cavity. A 2-D sheet oscillator within a 3-D rectangular void defect cavity are mode matched.

In another embodiment, the source is configured to generate narrow band radiation within the THz region of approximately 0.3 to 10 THz (1 mm to 30 microns). The oscillator has a length comparable to the desired emission wavelength to produce a discrete spectrum with at least one local peak in the specified narrowband radiation. The oscillator has a dimension of no greater than 100 nm in at least one non-resonant dimension to suppress vibrational modes in the specified narrow band. The cavity has a resonant dimension comparable to the desired emission wavelength. The narrowband radiation generated will typically have a bandwidth of less than 20% and more preferably less than 10% of the center wavelength to be useful in many imaging and spectroscopy applications.

In another embodiment, the source is configured to generate narrow band radiation within the IR region of approximately 10 to 300 THz (30 microns to 1 micron). The oscillator has a length comparable to the desired emission wavelength to produce a discrete spectrum with at least one local peak in the specified narrowband radiation. The oscillator has a dimension of no greater than 100 nm in at least one non-resonant dimension to suppress vibrational modes in the specified narrow band. The cavity has a resonant dimension comparable to the desired emission wavelength. The narrowband radiation generated will typically have a bandwidth of less than 20% and more preferably less than 10% of the center wavelength to be useful in many imaging and spectroscopy applications.

These and other features and advantages of the invention will be apparent to those skilled in the art from the following detailed description of preferred embodiments, taken together with the accompanying drawings, in which:

BRIEF DESCRIPTION OF THE DRAWINGS

FIGS. 1a and 1b are respectively diagrams of a radiation source using thermally powered low dimensional nano-scale oscillators in micro-scale coupled photonic crystal resonant defect cavities and an exemplary 1-D carbon nanotube oscillator;

FIG. 2 is a diagram of a thermally powered 1-D oscillator within a void defect cavity;

FIGS. 3a and 3b are plots of the discrete spectrum generated by a 1-D CNT oscillator and the cavity resonance of a void defect cavity in the band gap of the photonic crystal, respectively;

DETAILED DESCRIPTION OF THE INVENTION

Figure 4:
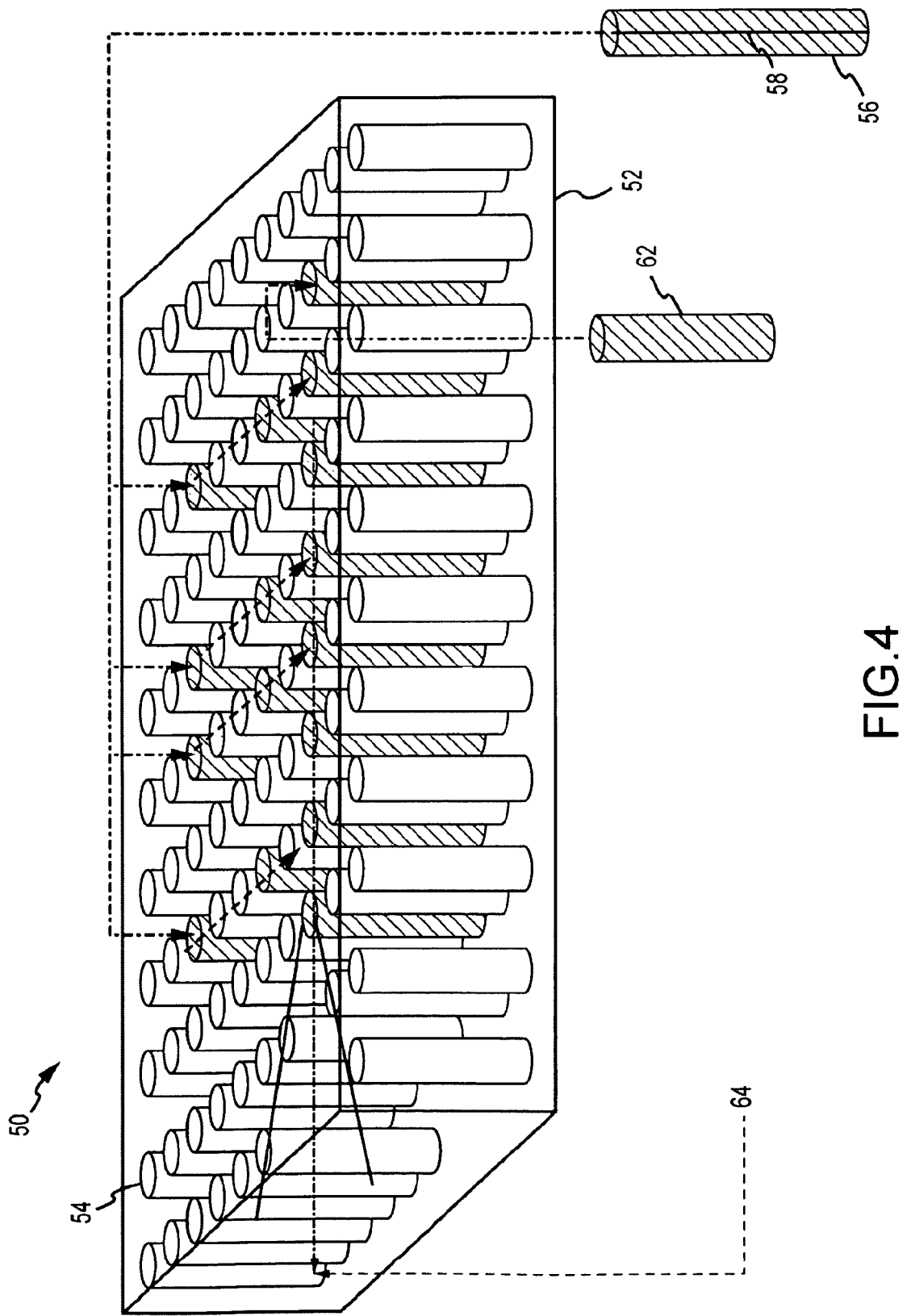
FIG. 4 is a diagram of a photonic crystal including a plurality of void defect cavities with 1-D oscillators and adjacent void defect cavities that form a waveguide to collect and transmit the electromagnetic radiation.

The present invention describes a thermally powered source of IR or THz radiation that combines low dimension nano-scale oscillators such as nano-wires and nano-tubes with micro-scale photonic crystal resonant cavities for efficient generation, coupling and transmission of electromagnetic radiation. The oscillators have M=0, 1 or 2 resonant dimensions on a micro-scale (approximately 1 um to approximately 1 mm) to emit radiation having a local peak at a desired wavelength in the IR or THz regions. The oscillators have at least one non-resonant dimension on a nano-scale (less than approximately 100 nm) to suppress vibration modes in that dimension and channel more thermal energy into the local peak. The photonic crystal defect cavities have N=1, 2 or 3 (N>M) resonant dimensions on the micro scale with lengths comparable to the length of the oscillator and the desired wavelength to exhibit a cavity resonant that overlaps the local peak to accept and transmit emitted radiation. The energy from multiple oscillator/defect cavities pairs can be collected and transmitted by a waveguide to a specified location where it is output. To improve coupling efficiency, the oscillators and defect cavities preferably exhibit a physical symmetry so that they are substantially "mode matched". The uniqueness of the present invention is the integration of efficient nano-scale emitters or oscillators and micro-scale photonic crystal coupling defect cavities and waveguides to efficiently couple and transmit narrowband radiation. The integration of nano-scale emitters with micro-scale photonic crystal defect cavities creates a new class of metamaterials that more efficient generate radiation.

An embodiment of a thermally powered source 10 is illustrated in FIGS. 1a and 1b, 2 and 3a-3b. The source emits narrowband radiation 12 centered about a specified center frequency 14 in the IR or THz spectral bands. Without loss of generality, this particular embodiment combines a 1-D (M=1) carbon nanotube (CNT) oscillator with a 3-D (N=3) void defect cavity. The source includes a photonic crystal 16 that exhibits a band gap 18 in the emission spectrum 20 of the crystal coincident with the specified narrow band (e.g. the narrow band lies within the band gap) such that a wavelength within the band gap is substantially confined in at least one dimension within the photonic crystal. A plurality of void defect cavities 22 are formed substantially within photonic crystal 16. The cavities exhibit a cavity resonance 24 within the band gap in N=3 dimensions. The resonant dimensions of the cavity are comparable to the wavelength associated with the center frequency, ranging from approximately 1 um to 1 mm to span the IR and THz bands. In this embodiment, the length $L_c$ and diameter $D_c$ of the defect cavity are comparable to the center wavelength. The photonic crystal and defect cavities are designed so that the cavity resonance coincides with the specified center frequency 14 of the narrowband radiation 12.

1-D CNT oscillators 26 are positioned substantially within respective void defect cavities 18. The oscillators generate electromagnetic radiation 28 having a spectrum 30 that exhibits at least one local peak 32 that resonates in M=1 dimensions 33. The oscillators concentrate more energy into the local peak 32 at the center frequency 14 than would be associated with the Planck distribution 34 for a three dimensional solid object. The resonant dimensions of the oscillator are comparable to the wavelength associated with the center frequency, ranging from approximately 1 um to 1 mm to span the IR and THz bands. A dimension of the oscillator or cavity that is "comparable to" the center wavelength may range, for example, between approximately 90% and 110% of the center wavelength depending on a variety of factors such as scatterer geometry. In this embodiment, the length $L_{osc}$ of the oscillator is comparable to the center wavelength and substantially the same length as the cavity. The non-resonant dimensions of the oscillator (e.g. the diameter $D_{osc}$) are on a nano-scale (<100 nm) so that vibrational modes are suppressed in the specified narrow band. The diameter of a typical CNT may range from 1 nm to 100 nm (single and multi-wall). The non-resonant dimension must be at least less than $1/10$ the center wavelength to suppress vibrational modes. In configurations that use nanowires or nanotubes, the non-resonant dimension may be less than $1/1000$ the center wavelength. The relative diameters of the oscillator $D_{osc}$ and cavity $D_c$ are not shown to scale.

The 1-D oscillator 26 can be more generally described as any three-dimensional (physical dimensions) object that resonates in only one dimension at the specified center frequency and suppresses vibrational modes in the other two dimensions. The oscillators are typically formed from conductive materials although semi-conductive materials may also work. As reported by Nemilentsau, CNTs provide a well-defined discrete spectrum with pronounced local peaks that are well-suited for our use. Nanotubes or nanowires formed from other materials such as Nitrogen, Boron, Titanium, Silicon, Germanium, Aluminum and Gallium may also provide suitable spectra. The characteristics of the nanotubes such as chirality, uniformity, junctions, etc. may be designed to enhance the emission performance of the oscillators. Nanotubes have very small diameters ranging typically from approximately 1 nm up to 100 nm, which will suppress vibrational modes for any specified narrow band in the IR or THz bands. Nanowires may also provide radiation spectra that are less smooth than the Planck distribution allowing the nanowires to be designed to channel more thermal energy into useful IR and THz frequencies.

Because the nano-scale oscillators 26 are very small, the amount of radiation they would produce from simple black-body radiation would be very small. Accordingly, means 36 heat the individual oscillators 26 to raise the intensity of electromagnetic spectrum 30. The spectrum emitted by the oscillators is independent of the photonic crystal structure and independent of temperature, depending only on the geometry of the oscillator. Thus, the oscillators can be heated to maximize emissions without affecting the spectrum. In this embodiment, means 36 includes a current source 38 that sources electrical current 40 through the oscillators to resistively heat the oscillators. Other techniques such as the use of microwave or laser beam heating could be used to selectively heat the oscillators. The oscillators could be formed from radioactive materials to provide heating. In a preferred embodiment of the invention, only the oscillators are directly heated, not the photonic crystal. The electrical current can be applied to only the oscillators. For microwave heating, the photonic crystal is formed from materials that are substantially transparent in the microwave band used to heat the oscillators. For laser beam heating, the laser can be controlled to selectively target only the oscillators. The mass of the oscillators is much less than the photonic crystal. Consequently, it takes much less energy to heat the oscillators to get the same or far greater radiation in the specified narrow band. Thus, the overall efficiency of the source is greatly enhanced.

The 1-D oscillators and 3-D void defect cavities are designed so that the cavity resonance 24 overlaps the local peak 32. The defect cavity accepts electromagnetic radiation 28 from the oscillator within the narrowband and transmits the radiation, effectively filtering the portion of the spectrum outside the cavity resonance. In other words, the defect cavity "resonates" with the local peak of the electromagnetic radiation generated by the oscillator. The oscillator and defect cavity will respectively generate and accept free propagating electromagnetic waves with first and second modes. To minimize losses these modes can be "matched". As will be illustrated for several cases in FIGS. 5-8, this can be accomplished by imposing a physical symmetry on the oscillator and defect cavity. In this embodiment, the 1-D CNT oscillator 26 (e.g. a long thin line source) and the 3-D cylindrical void defect cavity 22 are symmetrical, the mode generated by the oscillator matches the axial mode of the cylindrical cavity. In some instances the cavity and oscillator may be configured to extract a "preferred" mode. This is less efficient than mode matched but may be sufficient. For example, if the defect cavity were constrained to be rectangular and the oscillator 1-D, the cavity may force selection of a preferred mode.

A waveguide 42 substantially within the photonic crystal suitably collects electromagnetic radiation 28 in the narrowband of the cavity resonance from the plurality of void defect cavities and transmits the collected electromagnetic radiation 12 to a specified location 44 for emission, for example, via an antenna 46. The waveguide suitably comprises adjacent void defect cavities that do not include oscillators. The waveguide is tuned to the oscillator cavities, and thus suitably have similar geometry, dimensions, etc. The total surface area of the plurality of void defect cavities 22 that include oscillators is greater than the surface of the photonic crystal itself 12. Alternately, if the paired defect cavities 22 and oscillators 26 are in sufficient proximity they will resonate in unison. The radiation can be collected at specified location with mirrors or lenses external to the photonic crystal. An antenna at the location emits the collected radiation. In this case a waveguide is not required. The combination of low dimensional oscillators that can be designed to emit radiation concentrated in a local peak at a desired center frequency, efficiently heating only those low dimensional oscillators, mode matching the oscillators and defect cavities to efficiently couple the radiation in the local peak, collecting the radiation for a plurality (possibly many thousands) of oscillator/cavity pairs in a photonic crystal and guiding all of the radiation to a specified output provides for a very efficient and powerful source of IR and THz radiation. The marriage of nano-scale emitters and micro-scale photonic crystal structures from dissimilar technical fields can be configured to produce sufficient radiation to source macro-scale devices and applications.

A photonic crystal structure contains a periodic high-contrast modulation of the local index of refraction (or dielectric constant, for non-magnetic materials) in one, two or three dimensions (see for example J. D. Joannopoulos, R. D. Meade, and J. N. Winn, "Photonic Crystals: Molding the Flow of Light," Princeton: Princeton University Press (1995), or C. Lopéz, "Materials Aspects of Photonic Crystals," Advanced Materials 15, 1679 (2003)). Any two substances having sufficient contrast between their respective indices of refraction can be placed in a stable periodic arrangement with a particular geometry, spacing and shapes of the constituent substances to create a photonic crystal for a particular range of photon wavelengths. The photonic crystal may comprise materials, for example, silicon and air, but the photonic crystal may also comprise other materials, for example, SiN, $SiO_2$, plastics, metals, ceramics, composites, and many other materials, whether solid, liquid, or gas. Radiation propagating in such a structure will undergo multiple Bragg scattering from the lattice array and multiple Mie scattering off the individual scattering elements. Under certain conditions, the multiply-scattered waves interfere destructively, resulting in minimal transmission over a broad range of wavelengths, which is termed the "band gap" (a term borrowed from semiconductor physics). The photonic band gap is said to be complete when transmission is blocked for all angles of incidence and all polarization states within the wavelength band. The center wavelength of the band gap can be selected by controlling these parameters of the photonic crystal.

Resonant defect cavities in the periodic arrangement, which disturb the periodic structure of the crystal, exhibit an emission band within the band gap that accepts and transmits electromagnetic energy. In general, defect cavities may comprise an absence of material where material would be present, the presence of material where material would not otherwise be present, a different type of material, a different geometry of material or a void. The defect cavities are configured such that a narrow band of wavelengths within a band gap, as described earlier, encounters constructive interference when it enters a cavity, thus resulting in little loss within the cavity, i.e., the cavity may comprise a high Q factor. The cavity may be configured such that the wavelength of the local peak radiation of the oscillator encounters constructive interference within the cavity and may be leaked to other cavities, as described above.

Waveguide channels within the photonic crystal collect energy from multiple defect cavities and guide the energy to an output. One characteristic of multiple cavities is that they may be configured to resonate with one another by adjusting the size and the distance between the cavities; the size and location of the multiple cavities may be configured such that one cavity may couple its energy with the energy from another proximate cavity. In such an embodiment, one cavity effectively "leaks" electromagnetic radiation to the proximate cavity, and the amount of electromagnetic radiation leaked to the proximate cavity may be dependent on the amount of material between the two cavities. The oscillator/defect cavity pairs are coupled to defect cavities (sans the oscillator), which are in turn coupled to other adjacent defect cavities to guide the radiation to the output.

An embodiment of a photonic crystal 50 for use in the described radiation source is illustrated in FIG. 4. In this embodiment, photonic crystal 50 includes a medium 52 (e.g. a slab) having a first refractive index and a periodic array of cavities 54 (e.g. voids or rods) having a second refractive index different from the first. The geometry of the cavities, the spacing of the cavities, the modulation of the refractive indices etc. produce a band gap at a specified center frequency. Defect cavities 56, which disturb the periodic structure of the crystal, exhibit an emission band within the band gap that accepts and transmits electromagnetic energy. The use of thermally-powered oscillators within the defect cavities 56 places additional constraints on the cavities. First, the defect cavities are voids to allow for the placement of the oscillators 58 and to avoid direct conductive heating of the photonic crystal. If cavities 54 are voids, the void defect cavities will exhibit a different a geometry, e.g. different diameter. Second, to minimize losses the defect cavities may exhibit a symmetry with the oscillators to mode match. A waveguide 60 is formed of additional defect cavities 62 that are placed to accept radiation from defect cavities 56, collect the radiation and guide it to an output 64. As shown the additional defect cavities 62 are suitably identical to defect cavities 56 sans oscillator 58 to preserve the mode matched condition. However, these additional defect cavities are not required to have the same geometry or to be void defect cavities.

In another embodiment, the source is configured to generate narrow band radiation within the THz region of approximately 0.3 to 10 THz (1 mm to 30 microns). The oscillator has a length comparable to the desired emission wavelength to produce a discrete spectrum with at least one local peak in the specified narrowband radiation. The oscillator has a dimension of no greater than 100 nm in at least one non-resonant dimension to suppress vibrational modes in the specified narrow band. The cavity has a resonant dimension comparable to the desired emission wavelength. The narrowband radiation generated will typically have a bandwidth of less than 20% and more preferably less than 10% of the center wavelength to be useful in many imaging and spectroscopy applications.

In another embodiment, the source is configured to generate narrow band radiation within the IR region of approximately 10 to 300 THz (30 micron to 1 micron). The oscillator has a length comparable to the desired emission wavelength to produce a discrete spectrum with at least one local peak in the specified narrowband radiation. The oscillator has a dimension of no greater than 100 nm in at least one non-resonant dimension to suppress vibrational modes in the specified narrow band. The cavity has a resonant dimension comparable to the desired emission wavelength. The narrowband radiation generated will typically have a bandwidth of less than 20% and more preferably less than 10% of the center wavelength to be useful in many imaging and spectroscopy applications.

The symmetry of the low dimensional nano-scale oscillator and the micro-scaled photonic crystal defect cavity imposed by the mode matched condition is illustrated in FIGS. 5-9 for different combinations of oscillators and defect cavities.

Figure 5:
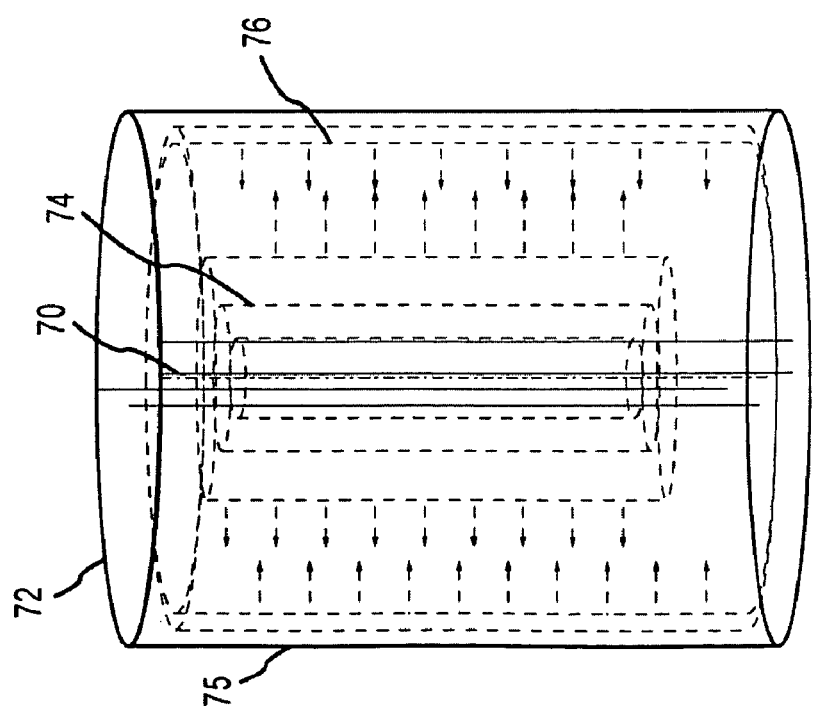
FIG. 5 is a diagram of a mode matched 1-D axial oscillator and a 3-D cylindrical void defect cavity.

As shown in FIG. 5, a plurality of 1-D oscillators 70 is positioned axially in a 3-D cylindrical void defect cavity 72. Each oscillator 70 emits radiation in cylindrical symmetric waves 74 (i.e. a cylindrical mode). The oscillators are spaced so that the waves reinforce each other and match modes. Although nanotubes and nanowires are themselves narrow cylinders it is possible that the 1-D oscillator could have, for example, a rectangular cross-section. However, because the radial dimensions are sufficiently small (<100 nm) the oscillator appears as a 1-D line source that emanates cylindrical symmetric waves. The walls 75 of cylindrical void defect cavity 72 reflect cylindrical waves 76. Consequently, the emitted waves 74 resonate in the cavity with minimal loss. A controlled amount of 'leakage' is provided to couple radiation out of the cavity, either directly for emission or more typically to adjacent defect cavities as part of a waveguide structure. In an alternate embodiment, a single oscillator 70 can be placed at the center of the cavity.

Figure 6A:
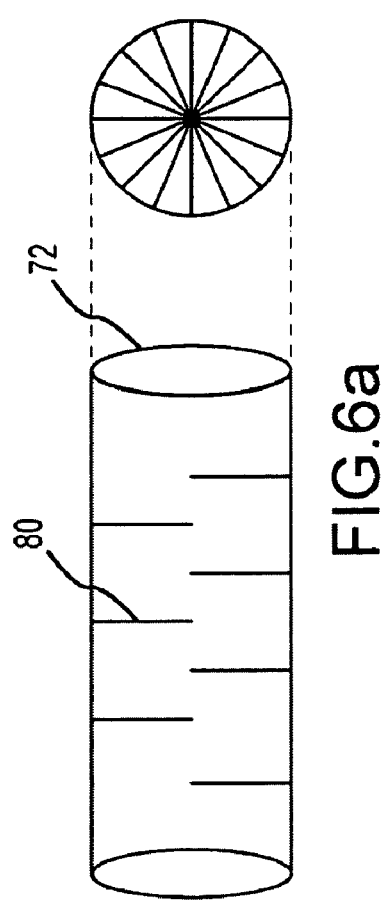
FIGS. 6a and 6b are diagrams of mode matched 1-D radial oscillators and a 3-D cylindrical void defect cavity and 1-D axial and radial oscillators and a 3-D cylindrical void defect cavity.
Figure 6B:
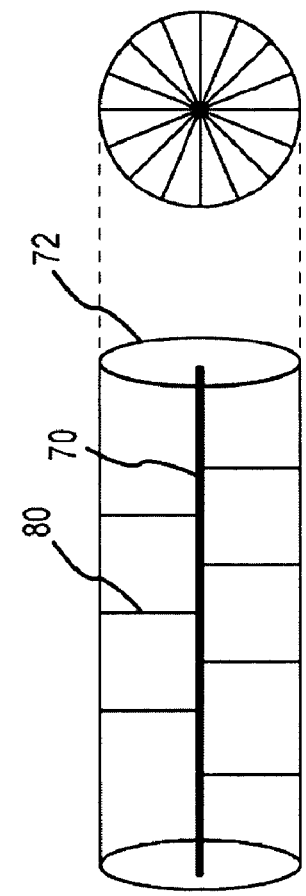

Cylindrical void defect cavity 72 accepts cylindrical mode electromagnetic waves in both an axial mode (of the type shown in FIG. 5) and a radial mode. As shown in FIG. 6a, a plurality of Oscillators 80 can be positioned radially in cavity 72 so that the emitted radiation in cylindrical symmetric waves is matched to the second radial mode of the cavity. The oscillators or "spokes" may start at the center of the cavity and extend to the walls, start at the center of the cavity and stop short of the walls or start at the walls and stop short of the cavity center. As shown in FIG. 6b, axial oscillator 70 and radial oscillators 80 can be configured to emit radiation that mode matches the axial and radial modes of the cavity, respectively.

Figure 7:
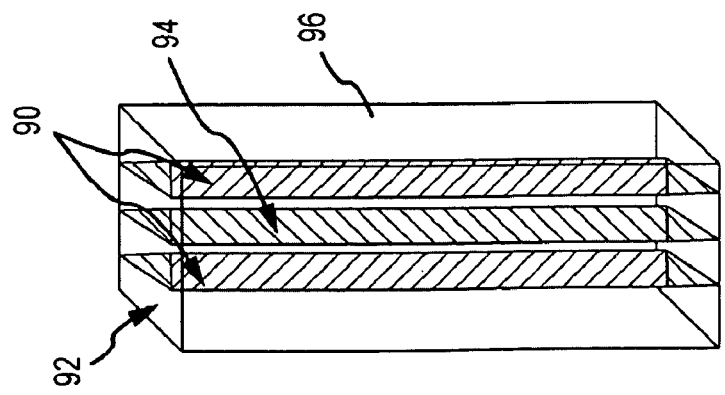
FIG. 7 is a diagram of a mode matched 2-D sheet oscillator and a 3-D cuboid void defect cavity.

As shown in FIG. 7, multiple 2-D sheet oscillators 90 are positioned in a 3-D cuboid void defect cavity 92. A "cuboid" is a rectangular box, essentially a cubic without the constraint that the height, length and depth are equal. The 2-D sheet oscillator has resonant dimensions in the plane of the sheet that are comparable to the center wavelength. The sheet is sufficient thin e.g. <100 nm, to suppress vibrational modes in the third dimension. Oscillator 90 emits radiation in planar symmetric waves 94. The walls 96 of cuboid void defect cavity 92 reflect planar waves. Consequently, the emitted waves 94 resonate in the cavity with minimal loss. The multiple oscillators are spaced so that the waves reinforce each other and match modes. Alternately, a single 2-D sheet oscillator could be positioned at the center of the cavity.

Figure 8C:
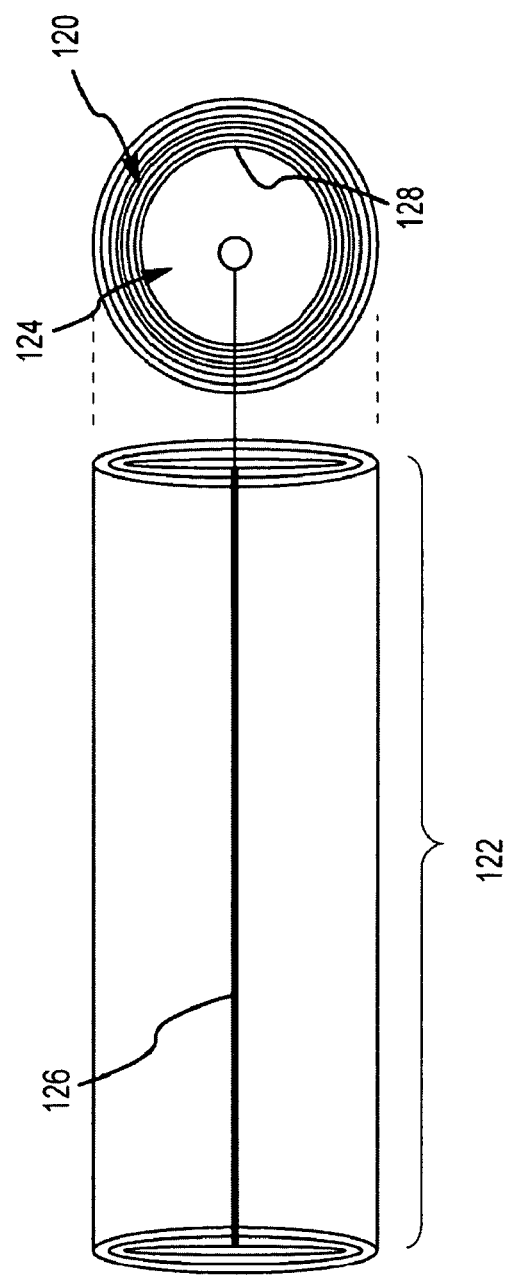
FIGS. 8a through 8c are diagrams of alternate embodiments of 1-D cylindrical oscillators in 2-D planar void defect cavities
Figure 8B:
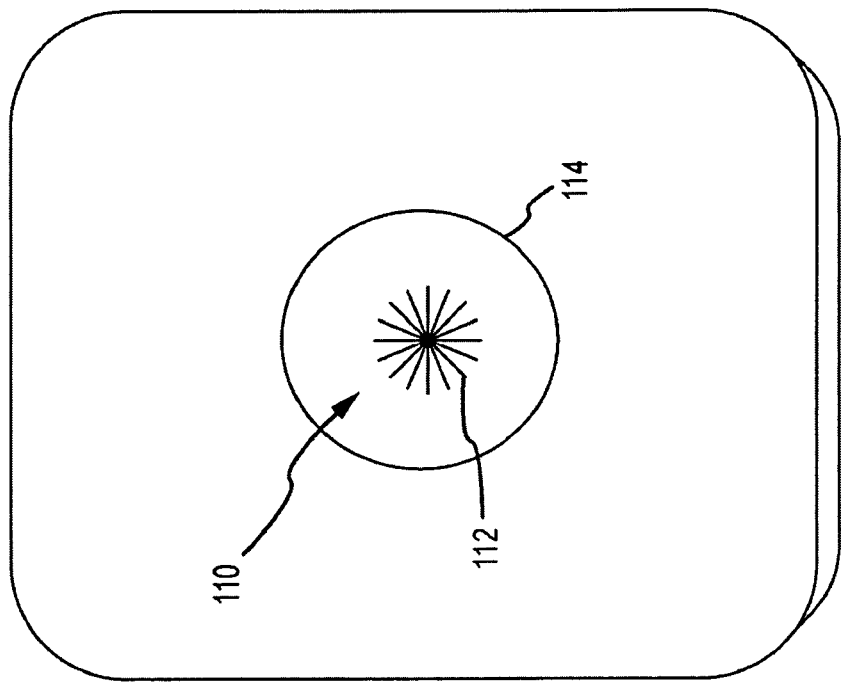
Figure 8A:
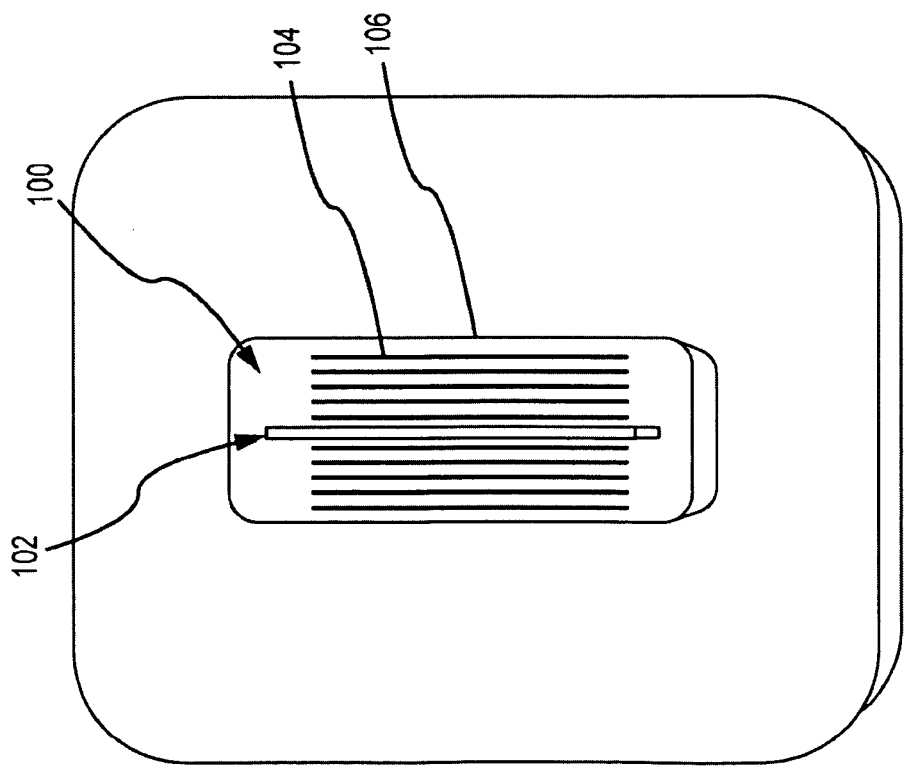

FIGS. 8a through 8c depict different embodiments of 1-D oscillators in 2-D void defect cavities. The 2-D void defect cavity has two resonant dimensions that are comparable to the center wavelength and a third non-resonant dimension that is sufficiently small (e.g. <100 nm) to suppress vibration modes. As shown in FIG. 8a, a 2-D void defect cavity 100 is a rectangular void. A 1-D oscillator 102 is positioned in the void along its long axis. Note, although the width or short-axis of cavity 100 is not the same length as the oscillator it is still 'comparable' to the wavelength. Comparable can be between approximately 50% of the wavelength up to approximately 150% of the wavelength. The oscillator emits radiation in cylindrical symmetric waves 104, which in a cross-sectional plane coincident with the 2-D void defect cavity appear as planar waves. The edges 106 of the cavity reflect the EM wave 104 to establish resonance in a mode matched condition. As shown in FIG. 8b, a 2-D void defect cavity 110 is a thin disk. 1-D oscillators 112 are positioned as spokes emanating radially from the center of the disk. The oscillators emit radiation in cylindrical symmetric waves, which are reflected by the inner edge 114 of the cavity to establish resonance in a mode matched condition. As shown in FIG. 8c, a photonic crystal 120 is constructed with a periodic structure that exhibits only a radial band gap. Therefore a cylindrical void 122 in the photonic crystal behaves like a stack of 2-D disks 124. A 1-D oscillator 126 positioned along the long axis of cylindrical void 122 emits cylindrical symmetric waves that are reflected by the edges 128 of each disk or slice to establish resonance in a mode matched condition.

Figure 9:
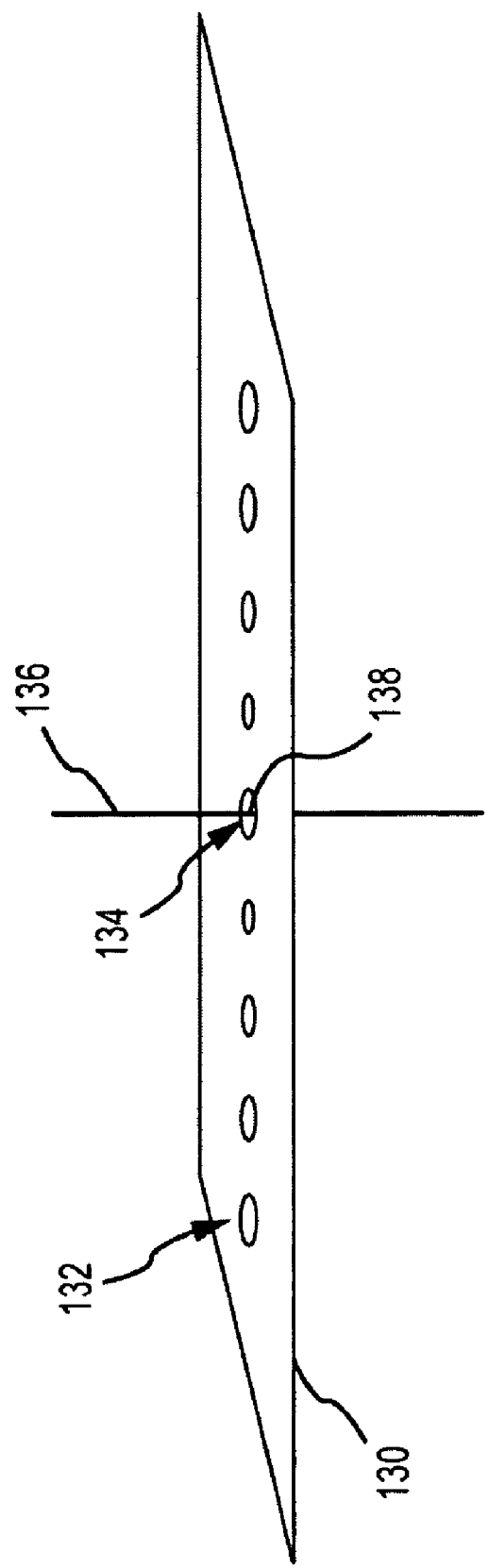
FIG. 9 is a diagram of a mode matched 0-D oscillator and a 1-D defect cavity.

FIG. 9 depicts an embodiment of a 0-D oscillator in a 1-D resonant defect cavity. A flat structure 130 with uniformly spaced holes 132 represents a one dimensional photonic crystal. The hole dimensions suddenly taper down to near zero from both sides with a single large hole in the center as a defect cavity 134. A nanowire 136 passing through the cavity 134 is designed to radiate only in the hole region by use of different materials along the wire. The end effect is a zero dimensional radiator 138 (the small radiating section of wire) inside a one dimensional defect cavity 134. The 0-D radiator emits electromagnetic radiation that resonates with the cavity resonance at the desired wavelength. The resonant condition effectively creates a local peak in the emission spectrum of the oscillator. In an alternate embodiment, the 0-D oscillator may comprise a point source such as a single atom or group of atoms as well as molecules such as Fullerenes. In this case, a heat source such as a microwave source or laser could be used to directly heat or excite the atom.

The radiation from a 3-D solid object is spherically symmetric in amplitude over $4\pi$ staradians. The low dimensional oscillators may be configured to emit radiation that is more directionally peaked (non-isotropic). For example, a 2-D emitter may emit primarily normal to the plane, a 1-D emitter may emit in a cylindrical lobe orthogonal to the line and a 0-D emitter may emit in a pattern determined by external electromagnetic conditions. The advantage of this is ease and efficiency of collecting the radiation.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

We claim:

1. A source of radiation for a specified band of wavelengths, comprising:
   a photonic crystal that exhibits a band gap coincident with the specified band such that a wavelength within the band gap is substantially confined in at least one dimension within the photonic crystal;
   at least one void defect cavity substantially within the photonic crystal that exhibits a cavity resonance within the band gap in N dimensions where N is an integer of value 1, 2 or 3;
   an oscillator substantially within the void defect cavity in the crystal, said oscillator resonating in M dimensions where M is an integer less than N of value 0, 1 or 2 to generate electromagnetic radiation having a spectrum that exhibits at least one local peak, one said local peak overlapping with said cavity resonance whereby the cavity accepts and transmits electromagnetic radiation in the local peak; and
   means for heating the oscillator to increase the electromagnetic radiation.

2. The source of radiation of claim 1, further comprising:
a plurality of said oscillators substantially within a respective plurality of said void defect cavities substantially within the photonic crystal, and
means for collecting electromagnetic radiation from the plurality of void defect cavities to a specified location.

3. The source of radiation of claim 2, wherein the total surface area of the plurality of void defect cavities is greater than the surface area of the photonic crystal.

4. The source of radiation of claim 2, wherein the means comprises a waveguide substantially within the photonic crystal that collects radiation from the plurality of void defect cavities and transmit the collected radiation to a specified location on the photonic crystal.

5. The source of radiation of claim 3, further comprising an antenna at the specified location to emit electromagnetic radiation in the specified band.

6. The source of radiation of claim 1, wherein the oscillator comprises an M=1 dimensional nanowire or nanotube.

7. The source of radiation of claim 6, wherein lengths of the oscillator and the void defect cavity in the resonant dimensions are approximately equal and comparable to wavelengths in the specified band and the void defect cavity has a diameter at least 1000 times greater than the diameter of the nanowire or nanotube.

8. The source of radiation of claim 1, wherein the lengths of the oscillator and the void defect cavity in the resonant dimensions where M=1 or 2 are approximately equal and comparable to wavelengths in the specified band.

9. The source of radiation of claim 1, wherein said oscillator generates electromagnetic radiation in a first mode and said void defect cavity accepts radiation in a second mode, said oscillator and cavity symmetrically configured so that said first and second modes substantially match.

10. The source of radiation of claim 9, wherein said void defect cavity comprises a cylindrical void that resonates in N=3 dimensions and said oscillator comprises a line source that resonates in M=1 dimension.

11. The source of radiation of claim 10, wherein the line source is positioned axially within the cylindrical void so that said first mode is substantially matched to a second axial mode of the cylindrical void.

12. The source of radiation of claim 10, wherein the line source is positioned radially within the cylindrical void so that said first mode is substantially matched to a second radial mode of the cylindrical void.

13. The source of radiation of claim 9, wherein said void defect cavity comprises a planar void that resonates in two dimensions and said oscillator comprises a line source that resonates in one dimension.

14. The source of radiation of claim 9, wherein said void defect cavity comprises a cuboid void that resonates in three dimensions and said oscillator comprises a thin sheet that resonates in two dimensions.

15. The source of radiation of claim 9, wherein said void defect cavity comprises an N=1 dimensional cavity and said oscillator comprises an M=0 oscillator.

16. The source of radiation of claim 1, further comprising a plurality of said oscillators substantially within the void defect cavity and spaced so that the generated electromagnetic radiation is reinforced.

17. The source of radiation of claim 1, wherein the specified band lies in the THz region of approximately 0.3-10 THz, said defect cavity and said oscillator having approximately the same length in a range of approximately 1 mm to approximately 30 microns, said oscillator having a dimension of no greater than approximately 100 nm in a non-resonant dimension and said cavity having a resonant dimension of approximately 1 mm to approximately 30 microns in that same dimension.

18. The source of radiation of claim 1, wherein the specified band lies in the IR region of approximately 10-300 THz, said defect cavity and said oscillator having approximately the same length in a range of approximately 30 microns to approximately 1 micron, said oscillator having a dimension of no greater than approximately 100 nm in a non-resonant dimension and said cavity having a resonant dimension of approximately 30 microns to approximately one micron in that same dimension.

19. A method of generating radiation in a specified band of wavelengths, comprising:
providing a plurality of oscillators that resonate in M dimensions where M is an integer of value 0, 1 or 2 to generate electromagnetic radiation having a spectrum that exhibits at least one local peak;
heating the oscillators to increase the electromagnetic radiation;
coupling the one said local peak of the oscillators' spectrums to respective void defect cavities substantially within a photonic crystal that exhibit a cavity resonance that overlap the local peak within a band gap coincident with the specified band in N dimensions where N is an integer greater than M of value 1, 2 or 3;
collecting the electromagnetic radiation in the local peak from the plurality of void defect cavities at a specified location;
and
transmitting the collected electromagnetic radiation.

20. The method of claim 19, where said oscillators generate electromagnetic radiation in a first mode and said void defect cavities accept radiation in a second mode, said oscillator and cavity symmetrically configured so that said first and second modes substantially match.

21. The method of claim 19, wherein the specified band lies in the THz region of approximately 0.3-10 THz, said paired defect cavity and said oscillator having approximately the same length in a range of approximately 1 mm to approximately 30 um, said oscillator having a dimension of no greater than approximately 100 nm in a non-resonant dimension and said cavity having a resonant dimension of approximately 1 mm to approximately 30 um in that same dimension.

22. The method of claim 19, wherein the specified band lies in the IR region of approximately 10-300 THz, said paired defect cavity and said oscillator having approximately the same length in a range of approximately 30 microns to approximately 1 micron, said oscillator having a dimension of no greater than approximately 100 nm in a non-resonant dimension and said cavity having a resonant dimension of approximately 30 microns to approximately 1 micron in that same dimension.

23. A source of radiation for a specified band of wavelengths in the THz (0.3-10 THz) or IR (10-300 THz) regions, comprising:
a photonic crystal that exhibits a band gap coincident with the specified band such that a wavelength within the band gap is substantially confined in at least one dimension within the photonic crystal;
a plurality of void defect cavities substantially within the photonic crystal, each said defect cavity exhibiting a cavity resonance within the band gap in N dimensions where N is an integer of value 2 or 3 and accepting electromagnetic radiation in a first mode, each of said N dimensions having a physical extent comparable to a center wavelength of the specified band of between approximately 1 micron and approximately 1 mm;

a plurality of nano-scale oscillators substantially within a respective one of the void defect cavities in the crystal, each said oscillator generating electromagnetic radiation in a second mode that is substantially matched to said first mode, said radiation having a spectrum that exhibits at least one local peak, each said oscillator resonating in M dimensions where M is an integer less than N of value 1 or 2, each of said M dimensions having a physical extent comparable to a center wavelength of the specified band between approximately 1 micron and approximately 1 mm and said at least one non-resonant dimensions having a physical extent less than approximately 100 nm, one said local peak overlapping with said cavity resonance whereby the cavity accepts and transmits the electromagnetic radiation in the local peak;

means for heating the oscillator to increase the electromagnetic radiation; and means for collecting electromagnetic radiation from the plurality of void defect cavities at a specified location.

24. The source of radiation of claim 23, wherein said oscillator generates electromagnetic radiation in a first mode and said void defect cavity accepts radiation in a second mode, said oscillator and cavity symmetrically configured so that said first and second modes substantially match.

* * * * *